United States Patent [19]

Geiser et al.

[11] 4,287,038

[45] Sep. 1, 1981

[54] PURIFICATION OF CHLOROPHENOLIC DERIVED COMPOUNDS

[75] Inventors: Edward M. Geiser, Downers Grove; Russell W. Johnson, Villa Park, both of Ill.

[73] Assignee: UOP Inc., Des Plaines, Ill.

[21] Appl. No.: 147,981

[22] Filed: May 8, 1980

[51] Int. Cl.³ .............................................. B01J 19/12
[52] U.S. Cl. ......................................... 204/158 R
[58] Field of Search ............ 204/158 R, 158 L, 158 P

[56] References Cited

U.S. PATENT DOCUMENTS

| 3,844,914 | 10/1974 | Murchison | 204/158 P |
| 4,212,717 | 7/1980 | Moore et al. | 204/158 L |

FOREIGN PATENT DOCUMENTS 2814126  10/1979  Fed. Rep. of Germany ....... 204/158 P

*Primary Examiner*—Howard S. Williams
*Attorney, Agent, or Firm*—James R. Hoatson, Jr.; Raymond H. Nelson; William H. Page, II

[57] ABSTRACT

Chlorophenolic derived compounds which may be used as herbicides and which contain a contaminant comprising 2,3,7,8-tetrachlorodibenzo-p-dioxin may be purified by subjecting a solution of the compound dissolved in a protic solvent to the emission from a light source having a wave length of from about 180 to about 350 nanometers, such as a laser beam, whereby the contaminant will be decomposed.

10 Claims, No Drawings

PURIFICATION OF CHLOROPHENOLIC DERIVED COMPOUNDS

This invention relates to a process for the purification of chlorophenolic derived compounds. More specifically, the invention is concerned with a process for decomposing contaminants such as 2,3,7,8-tetrachlorodibenzo-p-dioxin which are present in chlorophenolic derived compounds, the latter being used as herbicides or wood preservatives.

Commercial herbicides which are used to control unwanted plants such as weeds thus increasing the yields of desired products are used with increasing frequency. Of the herbicides which are employed a particular group of compounds are those which have been derived from chlorophenolic compounds. However, the chlorophenolic compounds generally contain contaminants, a specific contaminant which is present in these compounds comprising 2,3 7,8-tetrachlorodibenzo-p-dioxin (TCDD). Although the concentration of TCDD is commercial herbicides is relatively low, that is, less than about 50 ppb, the extreme toxicity which this compound possesses has raised some concern regarding the use of the chlorophenolic derived herbicides. It has been found that TCDD is extremely toxic for animals and relatively toxic for humans. The toxicity of this compound lies in the fact that it is both carcinogenic, that is, it possesses cancer forming properties, as well as being teratogenic, that is, it possesses properties which may lead to birth defects. Therefore, in order to employ these compounds as herbicides, it is necessary to purify the same by removing as much as possible of the toxic compounds.

The removal of the contaminating force from the chlorophenolic compounds may be accomplished by decomposing the offending compound, said decomposition usually being effected by a dechlorination of the compound to the trichloro-, dichloro- or monochloro-substituted dibenzo-p-dioxin. The removal of one or more chlorine atoms from the compound will result in a decrease of the toxicity of the compound, said dechlorination being due to the fact that the chlorine to carbon bond is the weakest bond present in said compound. Other forms of decomposition will include a rupture of the oxygen to chlorine bond thus destroying the dioxin portion of the molecule.

Heretofore the photodecomposition of TCDD by sunlight has been noted as well as the use of conventional ultraviolet light. However, this method of decomposing TCDD is relatively difficult to accomplish when it is present in a chlorophenolic derived compound such as 2,4,5-trichlorophenoxyacetic acid inasmuch as there is a relatively small difference in the ultraviolet peak positions of the two compounds. Thus, if conventional ultraviolet light or sunlight was used to photodecompose TCDD, it would also tend to decompose the host compound, namely, the 2,4,5-trichlorophenoxyacetic acid. However, by utilizing a light source of the type hereinafter set forth in greater detail, it is possible to decompose the undesirable contaminant such as 2,3,7,8-tetrachlorodibenzo-p-dioxin without appreciably affecting the host compound.

It is therefore an object of this invention to provide a process for removing undesired contaminants from chlorophenolic derived compounds.

A further object of this invention is to provide a process for the removal of undesirable contaminants from chlorophenolic derived compounds by utilizing a light source which possesses a relatively narrow wave length.

In one aspect an embodiment of this invention is found in a process for the removal of a contaminant comprising 2,3,7,8-tetrachlorodibenzo-p-dioxin from a chlorophenolic derived compound which comprises subjecting a solution of said compound dissolved in a protic solvent to the emission from a light source having a wave length in the range of from about 180 to about 350 nanometers, and recovering the purified chlorophenolic derived compound.

A specific embodiment of this invention is found in the process for the removal of 2,3,7,8-tetrachlorodibenzo-p-dioxin from 2,4,5-trichlorophenoxyacetic acid by subjecting a solution of said acid dissolved in methyl alcohol to the emission from a laser beam having a wave length in the range of from about 180 to about 350 nanometers, and recovering the purified 2,4,5-trichlorophenoxyacetic acid.

Other objects and embodiments will be found in the following further detailed description of the present invention.

As hereinbefore set forth the present invention is concerned with a process for the purification of chlorophenolic derived compounds containing contaminants such as polychlorodibenzo-p-dioxin compounds. The purification of the chlorophenolic derived compound is effected by subjecting a solution of said compound dissolved in a protic solvent to emission from a high quality light source. In the preferred embodiment of the invention, the high quality light source will possess a wave length in the range of from about 180 to about 350 nanometers ($10^{-9}$ meters). One particularly preferred light source comprises a laser beam, said term "laser" being an abbreviation for light amplification by stimulated emission of radiation. The use of a laser beam to effect the purification by means of photodecomposition of the contaminant possesses two advantages which are relevant to the purification, said advantages comprising spectral purity and power density. The advantage of the spectral purity which is a narrow band width is necessary in order to induce the photodecomposition of the contaminant without an appreciable decomposition of the chlorophenolic derived compound. That is, the light source may preferably comprise a narrow band pass so that the molecule which is being affected would be subjected to the intensity of radiation at the proper wave length. The advantage which lies in the power density of the laser radiation is desirable inasmuch as the contaminant is usually present in the host compound in a relatively low concentration, that is, less than about 50 and often less than about 20 ppb.

The light source which possesses a wave length within the range hereinbefore set forth may be obtained from any conventional type of laser. The laser which consists of a reservoir of active atoms which can be excited, a pump source to excite the available active atoms and a partially reflective resonant capacity to contain and control the light which is emitted from the excited atoms may be either solid state, gas, liquid, semiconductor or chemical in nature. Examples of solid state lasers which consist of a crystalline or glass host and a doping additive which is the reservoir of active ions will include synthetic ruby with a chromium dopant, synthetic garnet such as yttrium-aluminum-garnet with dopants such as neodymium, erbium, holmium, etc., or glass with a neodymium, erbium or holmium dopant;

gas lasers consisting of an optically transparent tube filled with a single gas or mixture of gases such as argon, krypton, nitrogen, carbon dioxide, helium-neon, etc.; semi-conductor lasers such as gallium-arsenic, gallium-aluminum-arsenic, lead-tin-tellurium, etc. It is to be understood that the aforementioned examples of lasers are only representative of the type of beams which may be employed and that the present invention is not necessarily limited thereto.

Examples of chlorophenolic derived compounds which are currently employed as herbicides and wood preservatives and which will contain toxic contaminants which must be removed prior to their use thereof, will include 2,4,5-trichlorophenoxyacetic acid (2,4,5-T); 2,4-dichlorophenoxyacetic acid (2,4-D); 4-chloro-2-methylphenoxyacetic acid (MCPA); 2-(2,4-dichlorophenoxy)propionic acid (2,4-DP); 2-(4-chloro-2-methylphenoxy)propionic acid (MCPP); 2-(2,4,5-trichlorophenoxy)propionic acid (2,4,5-TP); 4-(4-chloro-2-methylphenoxy)butyric acid (MCPB); pentachlorophenol, etc. As hereinbefore set forth by utilizing the emission from a light source such as a laser beam, it is possible to obtain an increased efficiency in the photodecomposition of the contaminant without a concomitant photodecomposition of the host compound.

The purification of the chlorophenolic derived compound of the type hereinbefore set forth is effected by subjecting a solution of the compound dissolved in a protic solvent using the emission from the high quality light source hereinbefore discussed. Examples of protic solvents which may be employed will include low molecular weight alcohols such as methyl alcohol, ethyl alcohol, n-propyl alcohol, isopropyl alcohol, etc., or low molecular weight carboxylic acids such as formic acid, acetic acid, propionic acid, butyric acid, etc. By utilizing these protic solvents, it is possible to effect a thorough dissolution of the chlorophenolic derived compound in the solvent and thus permit a more thorough exposure of the compound to the emission from the light rays. In addition, the protic solvent also provides a proton which assists in the removal of chlorine atoms by the formation of HCl. In the preferred embodimennt of the invention the purification of the compound is effected at ambient temperatures (20°-25° C.) and atmospheric pressure although it is also contemplated within the scope of this invention that other reaction conditions such as elevated or reduced temperatures and pressures may be employed, although not necessarily with equivalent results.

The process for the purification of the chlorophenolic derived compound is effected by placing a solution of the compound dissolved in a protic solvent of the type hereinbefore set forth in an appropriate apparatus. In the preferred embodiment of the invention the apparatus in which the solution is placed will comprise a quartz cell. The quartz is used due to the fact that it will not absorb light and is optically transparent in the region of interest. This is in contrast to other transparent apparatus such as Pyrex which will absorb light below about 350 nanometers. The solution is then subjected to irradiation from a light source which possesses a wave length below about 350 nanometers and preferably in a range of from about 180 to about 350 nanometers. The size of the apparatus or container will be that which is sufficient to provide a path length (the distance through which light travels in the reaction zone) in a range of from about 1 mm to about 40 meters, and preferably from about 1 cm to about 1 m. It is also contemplated that the path length may be increased by the use of external means such as reflective coatings or reflective surfaces such as mirrors. The operating parameters under which this reaction is effected will include ambient temperatures and atmospheric pressures. However, it is also contemplated within the scope of this invention that subambient temperatures may be employed. These subambient temperatures will range from ambient down to the freezing point of the protic solvent which is employed. For example, when methyl alcohol is used as the protic solvent for the chlorophenolic derived compound, it is possible to operate at temperatures down to about $-97°$ C.; when ethyl alcohol is employed as the solvent, temperatures down to about $-114°$ C. may be employed. The use of subambient temperatures in the reaction may be advantageous inasmuch as the electronic transition peaks of the contaminant such as TCDD and the host compound such as 2,4,5-T may be separated due to the lowering of the temperature and thus increase the efficiency of the laser beam to decompose the contaminant without a concomitant decomposition of the host compound. The irradiation of the solution is effected for a period of time which may range from about 0.5 up to about 10 hours or more in duration, the period of irradiation being dependent upon the variables which are present including the host compound, the contaminant, the concentration of the contaminant in the host compound, the concentration of the host compound in the solvent, the temperature, etc. Upon completion of the irradiation period the purified chlorophenolic derived compound may then be recovered by conventional means and separated from the solvent, if so desired, by fractional distillation, crystallization, etc.

It is also contemplated within the scope of this invention that the purification of the chlorophenolic derived compound may be accomplished in a continuous manner of operation in which the solution of the chlorophenolic derived compound dissolved in a protic solvent and which contains an undesired contaminant is continuously charged to a quartz vessel and subjected to irradiation by a laser beam for a period of time sufficient to decompose the undesired contaminant, the residence time during which the compound is subjected to irradiation being determined by the flow rate at which said solution is charged to the quartz vessel. After passage through the quartz vessel for a predetermined period of time, said vessel being maintained at predetermined operating temperatures, the purified solution is continuously withdrawn and subjected to conventional means of separation whereby the desired compound is separated from the protic solvent and recovered.

The following examples are given for purposes of illustrating the process of this invention. However, it is to be understood that these examples are given merely for purposes of illustration and that the present invention is not necessarily limited thereto.

EXAMPLE I

In this example the use of a light source possessing a wave length other than that which may be utilized in the process of this invention was employed. A sample of 2,3,7,8-tetrachlorodibenzo-p-dioxin was diluted with a sufficient amount of absolute methyl alcohol to prepare a solution containing 10.1 ppm of the contaminant. This solution was then diluted with an additional amount of methyl alcohol containing 2,4,5-trichlorophenoxyacetic acid until the final solution contained 10% of the acid, 90% methyl alcohol and 0.524 ppm of TCDD. Thereafter 30 ml of this solution was placed in a quartz reaction cell and irradiated for a period of 7.25 hours by emission from an Oriel 500 watt mercury arc lamp focused onto an Oriel grating monochronometer equipped with a 280 micron (2mm band pass) fixed slit. The output from the monochronometer was directed into the reactor cell which was 10 cm in length equipped with a ground fitting and flexible tubing which was coupled with a methanol trap to avoid the possibility of contaminated vapors escaping into the air. In addition the cell was wrapped with aliminum foil to increase the effective path length. At the end of the 7.25 hours the sample was recovered and subjected to analysis, said analysis disclosing that the irradiated sample possessed a TCDD concentration of 0.39 ppm. This corresponded to a 25.6% decomposition of contaminant which corresponds to a quantum efficiency of about 0.52. This value uses the radiation absorbed by the TCDD rather than the total solution absorption. The efficiency of the mercury arc lamp emission was 0.0004%. By utilizing this type of light source, it is estimated that the electricity required for the removal of the contaminant, namely, 2,3,7,8-tetrachlorodibenzo-p-dioxin will range from 47.6 to 476 kilowatt hours/kilogram of 2,4,5-trichlorophenoxyacetic acid and that the utility cost for the purification at a rate of 3.5¢/kilowatt hour will range from $1.57 to $15.70/kilogram of the acid.

EXAMPLE II

In constrast to this, when utilizing a light source possessing a wave length in the range of from about 180 to about 350 nanometers such as a laser beam, the electricity required, as measured in kilowatt hours, to remove a major portion of the contaminant, namely, 2,3,7,8-tetrachlorodibenzo-p-dioxin from 2,4,5-trichlorophenoxyacetic acid will only be 0.95. Likewise, it is also estimated that the utility cost for removal of this contaminant using a base of 3.5¢/kilowatt hour will only be $0.033 or 3.3¢/kilogram of acid. In addition, it is also estimated that the efficiency of the laser beam wil be 1%.

It is therefore readily apparent that by comparing the efficiency, the electricity required and the utility cost to purify a phenolic derived compound such as 2,4,5-trichlorophenoxyacetic acid when utilizing a light source possessing a wave length within the range of from about 180 to about 350 nanometers to light sources which possess wave lengths outside of this range, the former will afford a more efficient and less costly method for the removal of the contaminant with the concomitant obtention of a compound which may be utilized in the commercial field.

The utilization of a light source such as a laser beam for treating other phenolic derived compounds such as 4-chloro-2-methylphenoxyacetic acid, pentachlorophenol, or 2-(2,4,5-trichlorophenoxy)propionic acid may also show similar results.

We claim as our invention:

1. A process for the removal of a contaminant comprising 2,3,-7,8-tetrachlorodibenzo-p-dioxin from a chlorophenolic derived compound which comprises subjecting a solution of said compound dissolved in a protic solvent to the emission from a light source having a wave length in the range of from about 180 to about 350 nanometers, and recovering the purified chlorophenolic derived compound.

2. The process as set forth in claim 1 in which the removal of said contaminant is effected at ambient temperatures and atmospheric pressures.

3. The process as set forth in claim 1 in which said light source comprises a laser beam.

4. The process as set forth in claim 1 in which said chlorophenolic derived compound is 2,4,5-trichlorophenoxyacetic acid.

5. The process as set forth in claim 1 in which said chlorophenolic derived compound is 2,4-dichlorophenoxyacetic acid.

6. The process as set forth in claim 1 in which said chlorophenolic derived compound is 4-chloro-2-methylphenoxyacetic acid.

7. The process as set forth in claim 1 in which said chlorophenolic derived compound is pentachlorophenol.

8. The process as set forth in claim 1 in which said chlorophenolic derived compound is 2-(2,4,5-trichlorophenoxy)propionic acid.

9. The process as set forth in claim 1 in which the protic solvent comprises methyl alcohol.

10. The process as set forth in claim 1 in which the protic solvent comprises ethyl alcohol.

* * * * *